United States Patent [19]

Rescalli et al.

[11] Patent Number: 4,874,474
[45] Date of Patent: Oct. 17, 1989

[54] PROCESS FOR DEHYDRATING A MIXTURE OF METHANOL AND HIGHER ALCOHOLS

[75] Inventors: Carlo Rescalli, San Donato Milanese; Riziero Ricci, Cortemaggiore; Adriano Scazzosi, Corbetta; Flavio Cianci, San Donato Milanese, all of Italy

[73] Assignee: Snamprogetti S.p.A., Milan, Italy

[21] Appl. No.: 176,457

[22] Filed: Apr. 1, 1988

[30] Foreign Application Priority Data

Apr. 2, 1987 [IT]  Italy ............................ 19938 A/87

[51] Int. Cl.$^4$ ............................................. E01D 3/14
[52] U.S. Cl. ............................ 203/18; 203/DIG. 23; 568/913
[58] Field of Search .................. 203/18, 19, DIG. 23; 568/913

[56] References Cited

U.S. PATENT DOCUMENTS 4,210,495  7/1980  Pinto .................................. 203/18
4,256,541  3/1981  Muller et al. ....................... 203/19

Primary Examiner—Frank Sever
Attorney, Agent, or Firm—Birch, Stewart, Kolasch & Birch

[57] ABSTRACT

A process is disclosed for the dehydration of a mixture of methanol and higher alcohols, containing 20 to 80% by weight of methanol, 1 to 60% by weight of at least a higher alcohol selected from those containing from 2 to 10 carbon atoms, 1 to 50% by weight of water and 0.1 to 10% by weight of hydrocarbons and/or of oxygen-containing organic compounds different from alcohols, which process comprises the following steps:

(a) feeding to a first rectification tower the mixture of methanol and higher alcohols to be dehydrated, a gaseous stream being discharged from the tower head, which contains a portion of the hydrocarbons and/or of the oxygen-containing organic compounds different from the alcohols; from a side point at a level higher than 2/3 of the tower height, a stream containing methanol and possibly ethanol being drawn; and from the tower bottom a stream being obtained with a methanol, and possibly ethanol, and having a content not larger than 10% by weight;

(b) separating at least once the stream obtained from the bottom of the first column into two phases, one of which being aqueous, and the other phase being organic;

(c) feeding the organic phase to a second tower of azeotropic distillation, using a liquid-vapor and liquid-liquid separation agent; at the bottom an anhydrous stream being obtained, which contains the higher alcohol(s); and from the tower head a stream being obtained, which contains methanol, possibly ethanol and/or propanol, water, and the separation agent used, which is added to the stream obtained from the bottom of the first tower; and (d) feeding the aqueous phase to a third rectification tower; from the bottom a stream being removed which contains water; and overhead a stream being recovered, which is enriched with methanol and higher alcohols, which is recycled by being added to the mixture of methanol and higher alcohols to be dehydrated before being fed to the first rectification tower.

18 Claims, 1 Drawing Sheet

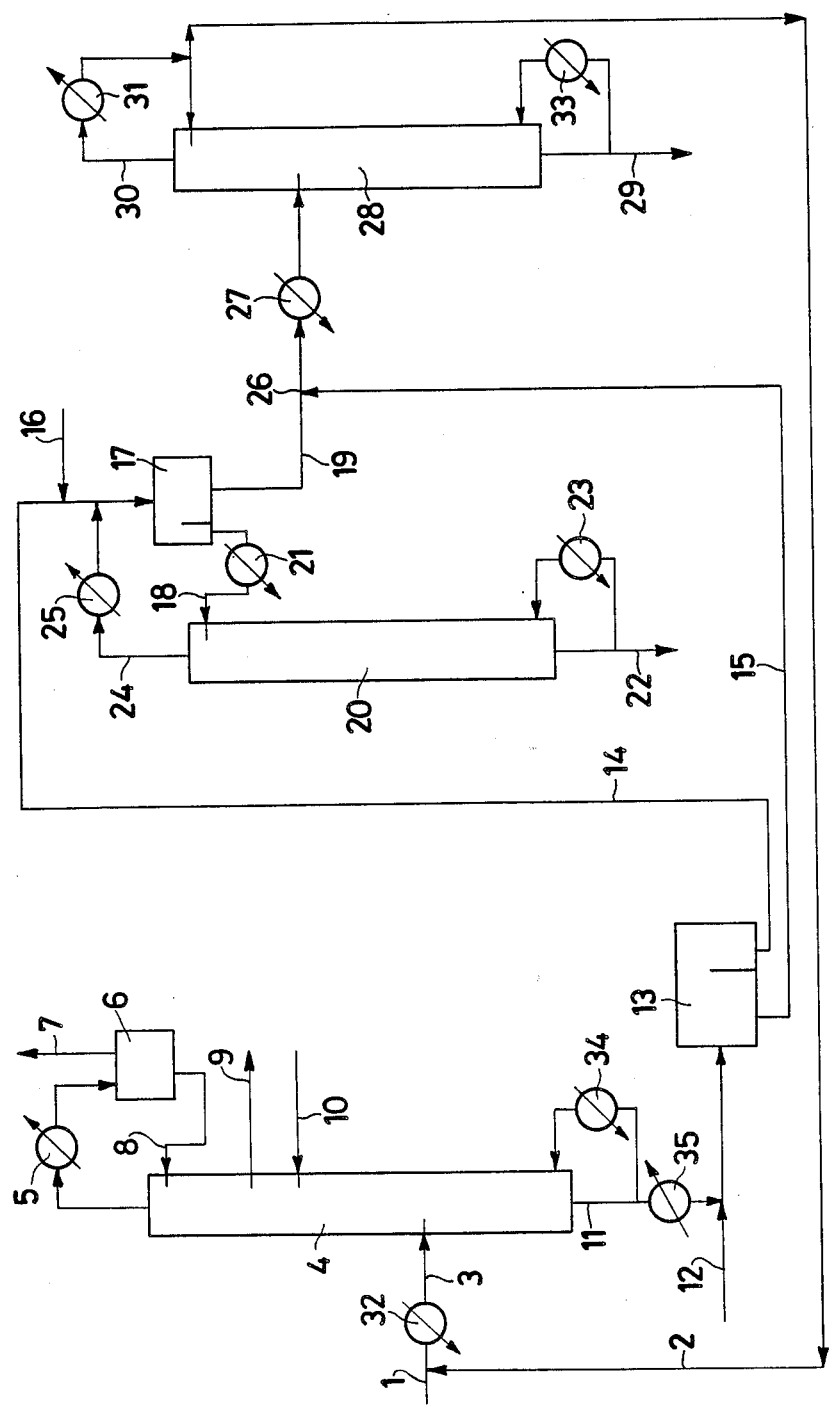

PROCESS FOR DEHYDRATING A MIXTURE OF METHANOL AND HIGHER ALCOHOLS

The present invention relates to a process for dehydrating a mixture of methanol and higher alcohols.

It is known that mixtures of methanol and higher alcohols can be used in mixture with gasoline, as fuel.

Normally, it is necessary that the mixtures of methanol and higher alcohols have a low water content. The alcohols form binary and/or multi-component azeotropic mixtures with water and/or the other organic compounds contained in the feedstock. Lowering the water content from a level of a few % to the level of thousand ppm is a difficult, and very expensive, operation.

The present art teaches to separate water from these mixtures by means of an azeotropic distillation with the use of cyclohexane, benzene, and other azeotropic agents.

A process has been found, which makes it possible to considerably lower the water content, even to levels lower than one thousand ppm, from mixtures of methanol and higher alcohols containing from 20 to 80%, preferably from 30 to 70% by weight of methanol, 1 to 60%, preferably 15 to 50% by weight of at least a higher alcohol selected from those having from 2 to 10 carbon atoms, 1 to 50%, preferably 10 to 30% by weight of water, and 0.1 to 10% by weight of hydrocarbons and/or oxygen-containing organic compounds different from alcohols (such as ethers, carbonyl compounds, esters, acids, heterocyclic compounds).

The process of the present invention comprises the following steps:

(a) feeding to a first rectification tower the mixture of methanol and higher alcohols to be dehydrated, a gaseous stream being discharged from the tower head, which essentially contains a portion of the hydrocarbons and/or of the oxygen-containing organic compounds different from the alcohols; from a side point at a level higher than ⅔ of the tower height, a stream essentially containing methanol and possibly ethanol being drawn; and from the tower bottom a stream with a methanol, and possibly ethanol, content not larger than 10% by weight, and preferably 0.1 to 5% by weight, being obtained;

(b) separating at least once the stream obtained from the bottom of the first column into two phases, one of which is aqueous, and the other phase being organic;

(c) feeding the organic phase to a second tower of azeotropic distillation, using a liquid vapor and liquid-liquid separation agent; at the bottom an anhydrous stream being obtained, which essentially contains the higher alcohol(s); and from the tower head a stream being obtained, which contains methanol, possibly ethanol and/or propanol, water, and the separation agent used, which is added to the stream obtained from the bottom of the first tower;

(d) feeding the aqueous phase to a third rectification tower; from the bottom a stream being removed which substantially contains water; and overhead a stream being recovered, which is enriched with methanol and higher alcohols, which is recycled by being added to the mixture of methanol and higher alcohols to be dehydrated before the latter is fed to the first rectification tower.

To the first rectification tower, an antifoaming solution, e.g., an aqueous-siliconic solution can be preferably fed to a side feed point.

It is recommended that to the stream obtained from the bottom of the first distillation tower an aqueous solution of NaOH and/or of other basic compounds be added. For example, carbonates, bicarbonates, hydroxides, phosphates of alkali or alkali-earth metals and/or nitrogen-containing compounds of the aminic, alkanolaminic, or heterocyclic type may be added in order to neutralize the acidic compounds possibly contained in the same stream.

The stream, as above specified, should be submitted at least once to a phase separation, in order to carry out the above operation of neutralization. In case two operations of phase separation are carried out, the first one is carried out by cooling, with an aqueous phase to be sent to the third rectification tower, and an organic phase to be submitted to a second phase separation being obtained.

To the stream to be submitted to the second phase separation, or to the single phase separation, an amount of water, preferably de-ionized water, should be preferably added, with such water amount being within the range of from 0.1 to 100% by weight relative to the same stream.

The water to be added may be a portion of the stream discharged from the bottom of the third tower.

The liquid-liquid separation agent, which also acts as the liquid vapor separation agent, can be selected, e.g., from cyclohexane, benzene, one or more hydrocarbon(s) having from 5 to 6 carbon atoms, or still other compounds which form a binary and/or multicomponent azeotropic mixture with water, either alone, or mixed with one another.

With regard to the pressures at which the three towers are operated, they should preferably be selected within a range of from 30 to 500 abs. kPa, more preferably of from 100 to 300 abs. kPa.

The invention is now disclosed in greater detail, with the aid of the diagram in the attached Figure, which represents a preferred embodiment, but which in no way should be considered as being limitative of the invention.

The mixture of methanol and higher alcohols to be dehydrated is fed to the facility by the stream 1 and, together with a recycled stream 2, is fed (3) to the rectification tower 4, after being heated in 32.

From the tower head, a gaseous stream outflows, which is condensed in 5 and is sent to the accumulator 6, from which a gaseous stream 7 is discharged, which essentially contains a portion of the hydrocarbons and/or of the oxygen-containing organic compounds different from alcohols, and an equilibrium liquid phase 8 is discharged and refluxed overhead the tower.

From a side point 9 at a level higher than ⅔ of the height of the same tower, an anhydrous stream is drawn, which essentially contains methanol, and possibly ethanol.

In order to prevent tower malfunctions due to the formation of foam, an antifoaming solution 10 is fed to the column.

From the bottom of the tower, a stream 11 is discharged, with a content of methanol, and possibly of ethanol, not larger than 10% by weight, with the tower being operated under relatively low stripping rate conditions.

To said stream 11, after that it is cooled in 35, an aqueous solution of NaOH 12 is added in order to neutralize the therein contained acidic compounds. The stream is then separated by cooling inside the phase separator 13 into an organic phase 14 and an aqueous phase 15.

The oragnic phase 14, after deionized water 16 is added thereto, is separated in the phase separator 17, to which the stream 24 is simultaneously fed, which is discharged from the condenser 25 of the second azeotropic tower 20, into an organic phase 18 and an aqueous phase 19.

The separated organic phase 18, after being heated in 21, is fed to the second azeotropic distillation tower 20, in which as the separating agent cyclohexane is used.

From the bottom of said second column an anhydrous stream 22 is obtained, which essentially contains higher alcohols, whilst from the tower head the stream 24 outflows, which contains methanol, ethanol, propanol cyclohexane and water. Said stream 24, as above mentioned, after being condensed in 25, is added to the organic phase 14, to which the aqueous stream 16 is possibly added too, before said stream 14 being separated in 17.

The aqueous phase 19 and the aqueous phase 15 are combined in 26, heated in 27 and fed to the rectification tower 28.

From said tower 28, from the bottom a stream 29 is obtained, which essentially contains wear, and overhead a stream 30 is obtained, which essentially contains alcohols and water, and is recycled, by means of the stream 2, by being added to the mixture of methanol and higher alcohols to be dehydrated 1.

By the reference numerals 31 and 33 the overhead condenser and the reboiler of the tower 28 are represented, and by the reference numerals 34 and 23 the reboilers of the tower 4 and of the tower 20 are respectively indicated.

EXAMPLE

The process is run according to the diagram of FIG. 1.

To a first rectification tower (4) (Stage glass tray tower, diameter=50 mm, equipped with adiabatic skirt; total trays=80; feed point=35th tray; $P_{head}$=atmospheric pressure; side draw point=70th tray) at T=50° C. a stream (3) is fed, which is constituted by raw MAS (a mixture of methanol and higher alcohols) (1) and a recycled stream (2); such streams are consituted by:

|  | (1) | (2) | (3) |
|---|---|---|---|
| Dimethylether | 5.1 g/h | — g/h | 5.1 g/h |
| Methanol | 1615.1 g/h | 0.6 g/h | 1615.7 g/h |
| Ethanol n-PrOH | 50.8 g/h | 18.7 g/h | 69.5 g/h |
| n-Propanol | 116.5 g/h | 42.1 g/h | 158.6 g/h |
| i-Butanol | 223.6 g/h | 27.2 g/h | 250.8 g/h |
| i-Amyl alcohol | 26.6 g/h | 1.4 g/h | 28.0 g/h |
| Other Organic components (Carbonyl compounds, Esters, Ethers, Acids, Hydrocarbons, Heterocyclic Compounds) | 218.9 g/l | 6.3 g/l | 252.2 g/l |
| Water | 516.3 g/l | 48.1 g/l | 564.4 g/l |
| CO$_2$ | 2.7 g/l | — g/l | 2.7 g/l |
| TOTAL STREAMS | 2775.6 g/l | 144.4 g/l | 2920.0 g/l |

From the accumulator (6) a gaseous stream (7) of 30.2 g/h is discharged, which contains all CO$_2$ and dimethylether contained in the feedstock, together with small amounts of methanol (9.1 g/h), other organic compounds (13.2 g/h) and water (0.1 g/h).

The liquid phase in equilibrium discharged from the same point (6,000 g/h) is totally refluxed: it is mostly constituted by methanol (3,812.1 g/h), with dimethylether (615.1 g/h), other organic compounds (1,600.4 g/h) and small water amounts (2.4 g/h).

From the 70th tray an anhydrous stream (9) is discharged (1,685.5 g/h), which is essentially constituted by all methanol and ethanol fed, and, more precisely:

| Methanol | 1606.0 g/h |
|---|---|
| Ethanol | 50.8 g/h |
| Other Organic Compounds (Carbonyl compounds, Esters, Ethers, Acids, Hydrocarbons, Heterocyclic compounds) | 28.4 g/h |
| Water | 1.3 g/h (0.08% by weight) |
| TOTAL STREAM | 1686.5 g/h |

In order to prevent possible tower malfunctions due to foam formation, at the level of the 55th tray an aqueous-siliconic solution at 1% by weight (10) is fed (3 g/h) to the tower.

In order to obtain such a high dehydration level, the tower is operated with a relatively low stripping rate of methanol and ethanol at the bottom: from this point of the tower (4), a stream (11) is discharged, which, by subsequent cooling to 30° C., is separated into an aqueous phase (15) and an organic phase (4); upstream the phase separator (13) an aqueous solution of NaOH (7% by weight) (12) is fed (20 g/h), in order to neutralize the acidic compounds contained in the stream (11).

The streams (11), (14) and (15) are characterized by:

|  | (11) | (14) | (15) |
|---|---|---|---|
| Methanol | 0.6 g/h | 0.4 g/h | 0.2 g/h |
| Ethanol | 18.7 g/h | 11.3 g/h | 7.4 g/h |
| n-Propanol | 158.6 g/h | 131.4 g/h | 27.2 g/h |
| i-Butanol | 250.8 g/h | 228.4 g/h | 22.4 g/h |
| i-Amyl alcohol | 28.0 g/h | 26.8 g/h | 1.2 g/h |
| Other Organic components (Carbonyl compounds, Esters, Ethers, Acids, Hydrocarbons Heterocyclic Compounds | 183.6 g/h | 177.3 g/h | 6.3 g/h |
| Water | 586.0 g/h | 119.7 g/h | 466.3 g/h |
| TOTAL STREAMS | 1226.3 g/h | 695.3 g/h | 531.0 g/h |

The so-obtained stream (14) is sent to a second azeotropic distillation tower (20) (a glass tower with packing; diameter=25 mm, equipped with an outer adiabatic skirt; packing=Raschig rings of glass, of 4×4 mm; tower height=2 m; feed point=overhead phase separator; $P_{head}$=atmospheric pressure) which, by using cyclohexane as the liquid vapor and liquid-liquid separation agent, makes it possible to remove any water still present inside the mixture of higher alcohols in question.

The organic phase (18) discharged from the phase separator (17) is recycled to the tower; the aqueous phase (19) discharged from the phase separator 17 makes it possible to completely separate the methanol and ethanol fed to the tower. In order to simplify such an operation, to the phase separator an additional stream (16) of 70 g/h of deionized water is sent; from the bottom of the tower (20), an anhydrous stream (22) of higher alcohols is discharged, which is free from cyclohexanol, as well as from methanol and ethanol. It contains the whole fed amount of n-propanol and i-butanol.

The streams concerning the tower (20) are constituted by:

|  | (18) | (19) | (22) |
|---|---|---|---|
| Methanol | — g/h | 0.4 g/h | — g/h |
| Ethanol | 42.6 g/h | 11.3 g/h | — g/h |
| n-Propanol | 158.8 g/h | 14.9 g/h | 116.5 g/h |
| i-Butanol | 223.6 g/h | 4.8 g/h | 223.6 g/h |
| i-Amyl alcohol | 26.6 g/h | 0.2 g/h | 26.6 g/h |
| Other Organic components (Carbonyl compounds, Esters, Ethers, Acids, Hydrocarbons Heterocyclic Compounds | 177.3 g/h | — g/h | 177.3 g/h |
| Water | 64.2 g/h | 189.6 g/h | 0.1 g/h |
| Cyclohexane | 450.0 g/h | — g/h | — g/h |
| TOTAL STREAMS | 1143.1 g/h | 221.2 g/h | 544.1 g/h |

The aqueous stream (19), combined with the analogous stream (15), is fed to a third end rectification tower (28), which makes it possible to recover the contained alcohols (30) as the overhead fraction, and then both water contained in the raw feedstock and water used in the same process to be removed as the bottom fraction (29). The tower (28) is constituted by two glass halftowers, (diameter=25 mm), equipped with an outer adiabatic skirt, packed with Raschig rings (4×4 mm) for a height of 70 cm respectively above and under the feed point; the tower is operated under an atmospheric $P_{head}$, and with an overhead reflux ratio of 1.8.

We claim:

1. A process comprising dehydrating a mixture of methanol and higher alcohols containing 20 to 80% by weight of methanol, 1 to 60% by weight of at least a higher alcohol selected from the group consisting of those having 2 to 10 carbon atoms, 1 to 50% by weight of water, and 0.1 to 10% by weight of hydrocarbons, oxygen-containing organic compounds different from alcohols, and combinations thereof, by the following steps:
   (a) feeding to a first rectification tower said mixture of methanol and higher alcohols to be dehydrated, a gaseous stream being discharged from the tower head which contains a portion of the hydrocarbons, oxygen-containing organic compounds different from the alcohols or combinations thereof; from a side point at a level higher than ⅔ of the tower height, a stream containing methanol, ethanol or combinations thereof being drawn; and from the tower bottom a stream with a methanol, ethanol or combinations thereof having a content not larger than 10% by weight being obtained;
   (b) separating at least once the stream obtained from the bottom of the first column into two phases, one of which is aqueous, and the other phase being organic;
   (c) feeding the organic phase to a second tower of azeotropic distillation, using a liquid-vapor and liquid-liquid separation agent; at the bottom an anhydrous stream being obtained, which contains the higher alcohols; and from the tower head a stream being obtained, which contains methanol, ethanol, propanol or combinations thereof, water, and the separation agent used, which is added to the stream obtained from the bottom of the first tower; and
   (d) feeding the aqueous phase to a third rectification tower; from the bottom a stream being removed, which contains water, and an overhead stream being recovered, which is enriched with methanol and upper alcohols, which is recycled by being added to the mixture of methanol and higher alcohols to be dehydrated before the latter is fed to the first rectification tower.

2. The process according to claim 1, wherein to the first rectification tower an antifoaming solution is fed through a side feed point.

3. The process according to claim 2, wherein the antifoaming solution is an aqueous-siliconic solution.

4. The process according to claim 1, wherein from the bottom of the first distillation column a steam is obtained, which has a content of methanol, ethanol or combinations thereof, in a range of 0.1 to 5% by weight.

5. The process according to claim 1, wherein to the stream obtained from the bottom of the first distillation tower a solution of basic compounds, nitrogen-containing compounds of the aminic, alkanolaminic, heterocyclic type or combinations thereof are added.

6. The process according to claim 5, wherein the basic compounds are selected from the group consisting of NaOH, carbonates, bicarbonates, hydroxides, phosphates of alkali, phosphates of alkali-earth metals and combinations thereof.

7. The process according to claim 1, which comprises two phase separations in step (b).

8. The process according to claim 7, wherein the first phase separation is carried out by cooling, with an aqueous phase to be sent to the third rectification tower, and an organic phase to be submitted to a second phase separation being obtained.

9. The process according to any one of claims 1 or 7, wherein water is added to the stream to be submitted to the one phase separation, or to the second phase separation.

10. The process according to claim 9, wherein the added water is deionized water.

11. The process according to claim 9, wherein the added water is a portion of the stream discharged from the bottom of the third tower.

12. The process according to claim 9, wherein 0.1 to 100% by weight water is added relative to the same stream.

13. The process according to claim 12, wherein 0.1 to 20% by weight water is added relative to the same stream.

14. The process according to claim 1, wherein the liquid-liquid separation agent is selected from at least one of the groups consisting of cyclohexane, benzene, a hydrocarbon having 5 to 6 carbon atoms, and combinations thereof.

15. The process according to claim 14, wherein the separating agent is cyclohexane.

16. The process according to claim 1, wherein the pressures under which the three towers operate are in a range of 30 to 500 abs. kPa.

17. The process according to claim 16, wherein the pressures are in a range of 100 to 300 abs. kPa.

18. The process according to claim 1, wherein said mixture comprises at least one compound selected from the group consisting of ethers, carbonyl compounds, esters, acids and heterocyclic compounds.

* * * * *